(12) United States Patent
Bell et al.

(10) Patent No.: US 12,109,070 B2
(45) Date of Patent: Oct. 8, 2024

(54) USING MACHINE LEARNING TECHNIQUES TO OBTAIN COHERENCE FUNCTIONS

(71) Applicant: THE JOHNS HOPKINS UNIVERSITY, Baltimore, MD (US)

(72) Inventors: Muyinatu Bell, Baltimore, MD (US); Alycen Wiacek, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 309 days.

(21) Appl. No.: 17/763,069

(22) PCT Filed: Sep. 28, 2020

(86) PCT No.: PCT/US2020/053070
§ 371 (c)(1),
(2) Date: Mar. 23, 2022

(87) PCT Pub. No.: WO2021/062362
PCT Pub. Date: Apr. 1, 2021

(65) Prior Publication Data
US 2022/0338841 A1    Oct. 27, 2022

Related U.S. Application Data

(60) Provisional application No. 62/907,356, filed on Sep. 27, 2019.

(51) Int. Cl.
*A61B 8/08* (2006.01)
*A61B 5/00* (2006.01)
(Continued)

(52) U.S. Cl.
CPC .......... *A61B 8/5207* (2013.01); *A61B 5/0095* (2013.01); *A61B 8/06* (2013.01);
(Continued)

(58) Field of Classification Search
CPC .......... A61B 5/0095; A61B 8/00; A61B 8/06; A61B 8/08; A61B 8/085; A61B 8/485;
(Continued)

(56) References Cited

U.S. PATENT DOCUMENTS

2017/0046839 A1    2/2017   Paik et al.
2017/0281121 A1*  10/2017  Dahl ...................... G16H 50/30
2020/0060652 A1*   2/2020  Dahl ........................ G06N 3/08

OTHER PUBLICATIONS

International Preliminary Report on Patentability in corresponding Application No. PCT/US2020/053070 mailed on Mar. 15, 2022, 5 pages.
(Continued)

*Primary Examiner* — Amelie R Davis
(74) *Attorney, Agent, or Firm* — MH2 Technology Law Group LLP

(57) ABSTRACT

A computer-implemented method for training and using a neural network to predict a coherence function includes: training a neural network by mapping a plurality of different sets of training input samples to respective coherence function truths to generate a trained neural network; receiving an operational input sample; inputting the operational input sample into the trained neural network; obtaining, from the trained neural network, a coherence function mapped to the operational input sample in response to the inputting the operational input sample into the trained neural network; and executing a computer-based instruction based on obtaining the coherence function. The coherence function may be used to differentiate solid masses from fluid-filled masses.

20 Claims, 10 Drawing Sheets

(51) Int. Cl.
    *A61B 8/06*         (2006.01)
    *G01S 7/52*         (2006.01)
    *G01S 15/89*       (2006.01)

(52) U.S. Cl.
    CPC .......... *A61B 8/485* (2013.01); *G01S 7/52026* (2013.01); *G01S 7/52046* (2013.01); *G01S 15/8915* (2013.01)

(58) Field of Classification Search
    CPC ... A61B 8/5207; A61B 8/5223; A61B 8/5269; G06N 3/08; G06F 30/27; G01S 7/52046
    See application file for complete search history.

(56) References Cited

OTHER PUBLICATIONS

Belugin, M. (RU Authorized Officer), International Search Report and Written Opinion issued Dec. 17, 2020 in corresponding International Application No. PCT/US2020/053070, 8 pages.

\* cited by examiner

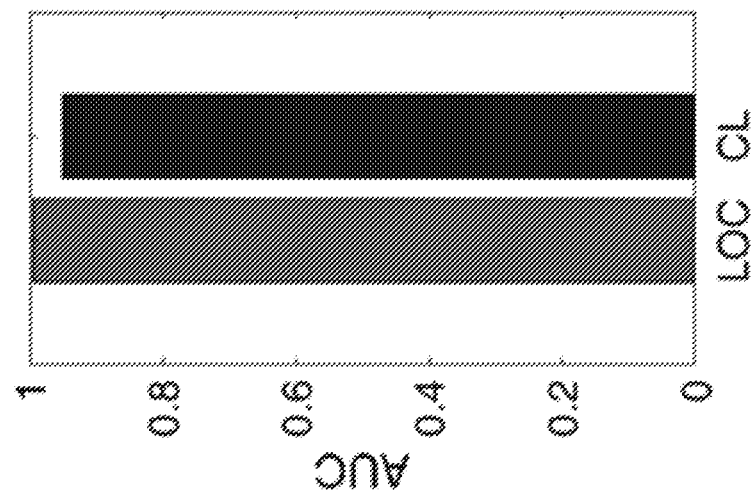
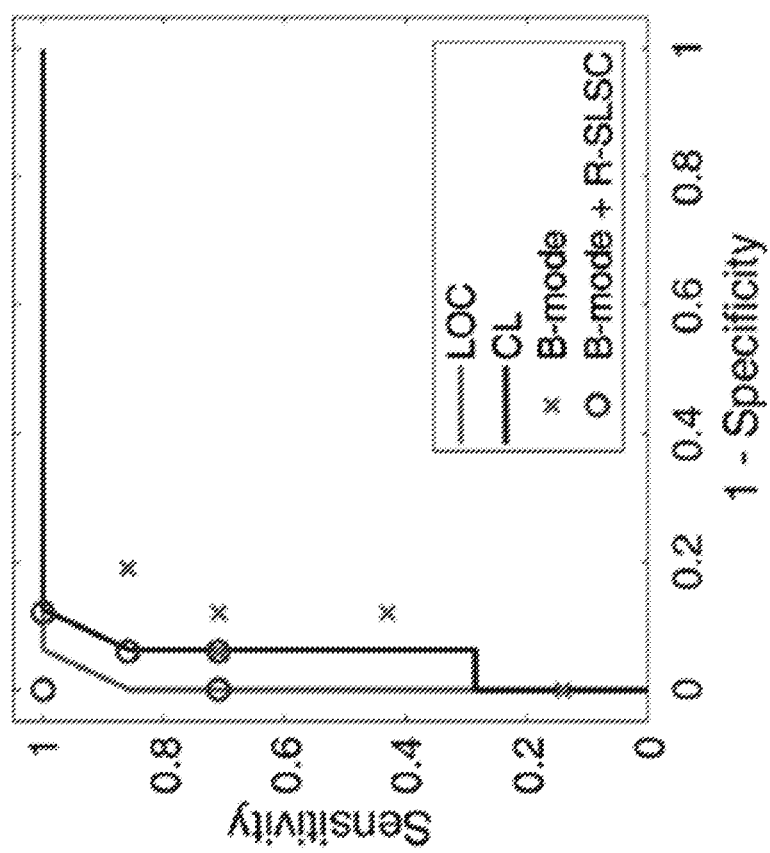
FIG. 5A
FIG. 5B

Fig. 6. (a) Processing times, FLOPs, and image-to-image correlations as functions of the number of samples (i.e., lateral × axial samples) included in each SLSC implementation (i.e., CPU, GPU, or DNN SLSC). Example images created with resampling factors of (b) 1/2 and (c) 1/4.

| Layer  | Type            | Size    | Activ. |
|--------|-----------------|---------|--------|
| Input  | -               | 7 x 64  | -      |
| 1      | Fully Connected | 7 x 64  | ReLU   |
| 2      | Fully Connected | 7 x 128 | ReLU   |
| 3      | Fully Connected | 7 x 128 | ReLU   |
| 4      | Fully Connected | 7 x 64  | Tanh   |
| Output | Average Pool    | 1 x 64  | -      |

FIG. 7

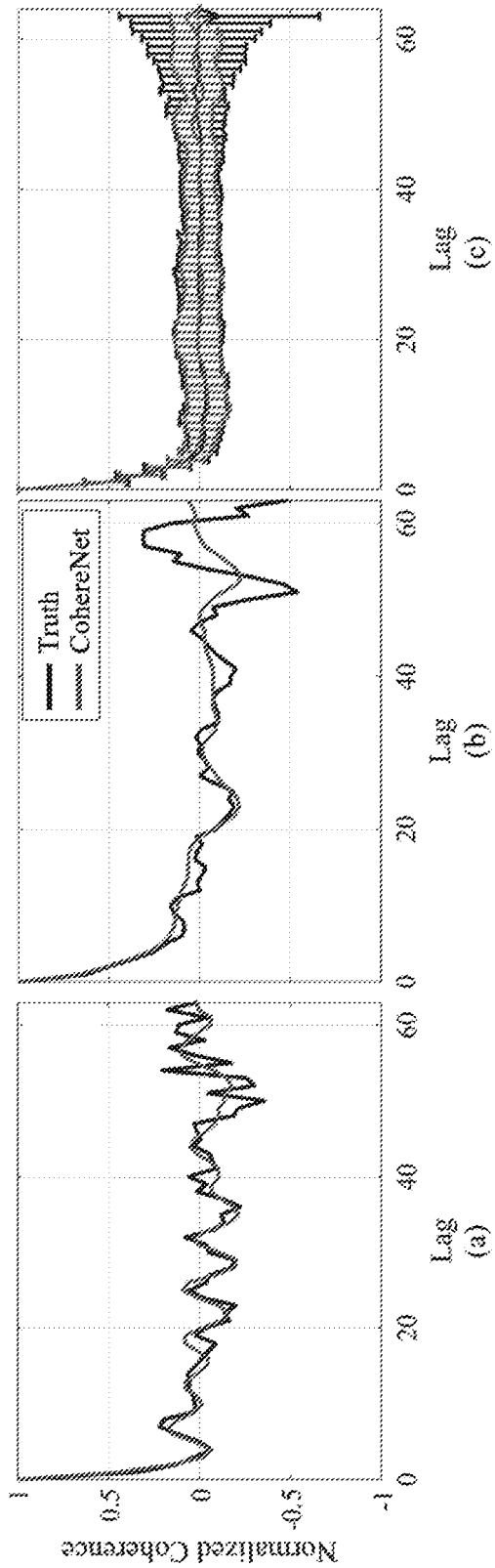

Figure 9. Example coherence function truths and coherence functions generated by CohereNet taken from locations where (a) the CohereNet output matches well with the truth, (b) the CohereNet output is smoother compared to the truth and the best match with the truth is obtained at lags <25 as a result of the Gaussian weighted mean square error loss function, and (c) the coherence function outputs are averaged over multiple axial and lateral positions (i.e., mean ± standard deviation coherence function of a 1 mm × 1 mm region surrounding the focus of *in vivo* breast data).

USING MACHINE LEARNING TECHNIQUES TO OBTAIN COHERENCE FUNCTIONS

CROSS-REFERENCE TO RELATED APPLICATIONS

This application is a national stage entry from International Application No. PCT/US2020/053070, filed on Sep. 28, 2020, published as International Publication No. WO 2021/062362 A1 on Apr. 1, 2021, and claims priority to U.S. Provisional Patent Application 62/907,356, which was filed on Sep. 27, 2020, all of which are incorporated herein by reference in their entireties.

BACKGROUND

Short-lag spatial coherence (SLSC) imaging is a beamforming technique for medical ultrasound imaging. Different from traditional beamforming methods, SLSC imaging displays the spatial coherence rather than the magnitude of the received signals from an array of sensors. Compared with conventional B-mode methods, SLSC imaging can better detect lesions inside tissues and distinguish between fluid-filled masses and solid masses. In addition, SLSC imaging can provide satisfactory contrast and lesion detectability even under a low signal-to-noise (SNR) condition. Previous research has proven that SLSC imaging can be applied to clinical research and has the potential of obtaining better image quality.

SUMMARY

In one example aspect, a computer-implemented method for training and using a neural network to predict a coherence function includes: training a neural network by mapping a plurality of different sets of training input samples to respective coherence function truths to generate a trained neural network; receiving an operational input sample; inputting the operational input sample into the trained neural network; obtaining, from the trained neural network, a coherence function mapped to the operational input sample in response to the inputting the operational input sample into the trained neural network; and executing a computer-based instruction based on obtaining the coherence function.

In another example aspect, a computer program product includes a computer readable storage medium having program instructions embodied therewith. The program instructions are executable by a computing device to cause the computing device to perform operations including: receiving an operational input sample; inputting the operational input sample into a trained neural network; obtaining, from the trained neural network, a coherence function mapped to the operational input sample in response to the inputting the operational input sample into the trained neural network; and executing a computer-based instruction based on obtaining the coherence function.

In another example aspect, a system includes a processor, a computer readable memory, a non-transitory computer readable storage medium associated with a computing device, and program instructions executable by the computing device to cause the computing device to perform operations including receiving an operational input sample; inputting the operational input sample into a trained neural network that maps a plurality of different sets of input samples to one or more coherence functions; obtaining, from the trained neural network, a coherence function mapped to the operational input sample in response to the inputting the operational input sample into the trained neural network; and executing a computer-based instruction based on obtaining the coherence function In another example aspect, a system includes a neural network trained in software by mapping a plurality of different sets of training input samples to respective coherence function truths. The trained network may be implemented in hardware (e.g., one or more field-programmable gate arrays, or FPGAs) associated with a computing device to perform operations including: receiving an operational input sample; inputting the operational input sample into the trained neural network; obtaining, from the trained neural network, a coherence function mapped to the operational input sample in response to the inputting the operational input sample into the trained neural network; and executing a computer-based instruction based on obtaining the coherence function.

BRIEF DESCRIPTION OF THE DRAWINGS

FIGS. 5A and 5B illustrate a receiver operator characteristic (ROC) curve for detection of fluid-filled masses with individual readers performance for comparison, and the associated area under the ROC curve (AUC) for lag-one coherence (LOC) and coherence length (CL).

FIG. 7 illustrates an architecture of a neural network, in accordance with aspects of the present disclosure.

FIG. 9A illustrates example coherence function truths and coherence functions generated by the trained neural network taken from locations where the neural network output matches within a threshold of the truth.

FIG. 9B, illustrates an example when the neural network output is smoother compared to the truth.

FIG. 9C illustrates the coherence function outputs averaged over multiple axial and lateral positions.

DETAILED DESCRIPTION

Figure 1:
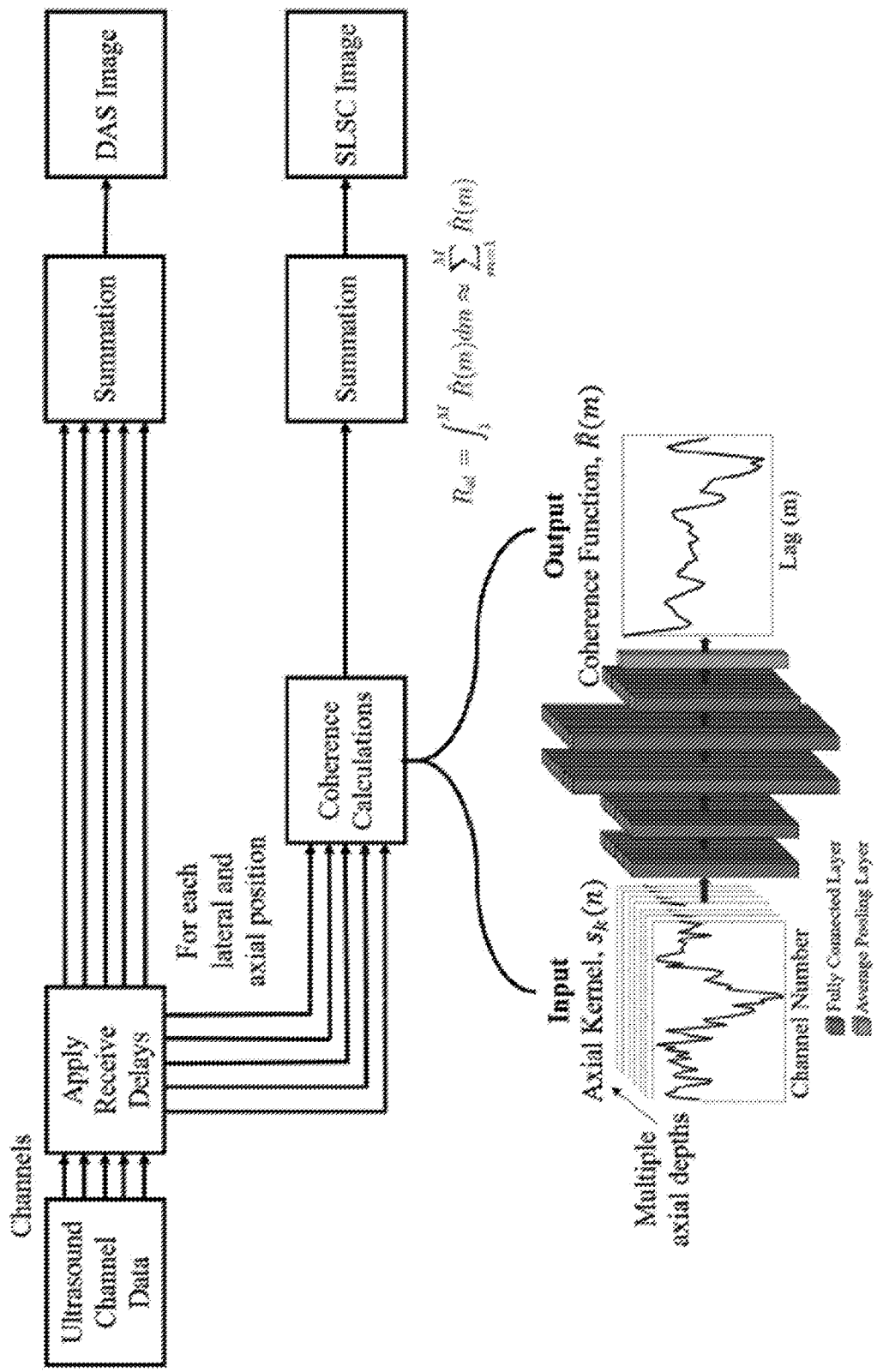
FIG. 1 illustrates an overview of an example implementation as described herein.

Certain embodiments of the disclosure will hereafter be described with reference to the accompanying drawings, wherein like reference numerals denote like elements. It should be understood, however, that the accompanying drawings illustrate only the various implementations described herein and are not meant to limit the scope of various technologies described herein. The drawings show and describe various embodiments of the current disclosure.

Spatial coherence functions may be used in a variety of coherence-based beamforming applications. For example, spatial coherence functions may be used for short-lag spatial coherence (SLSC) beamforming to produce SLSC images from ultrasound or ultrasound-derived image source data. Ultrasound-derived data includes any data received by ultrasonic sensors such as photoacoustic data. Spatial coherence functions may be used in a variety of other coherence-based beamforming applications.

Figure 6:
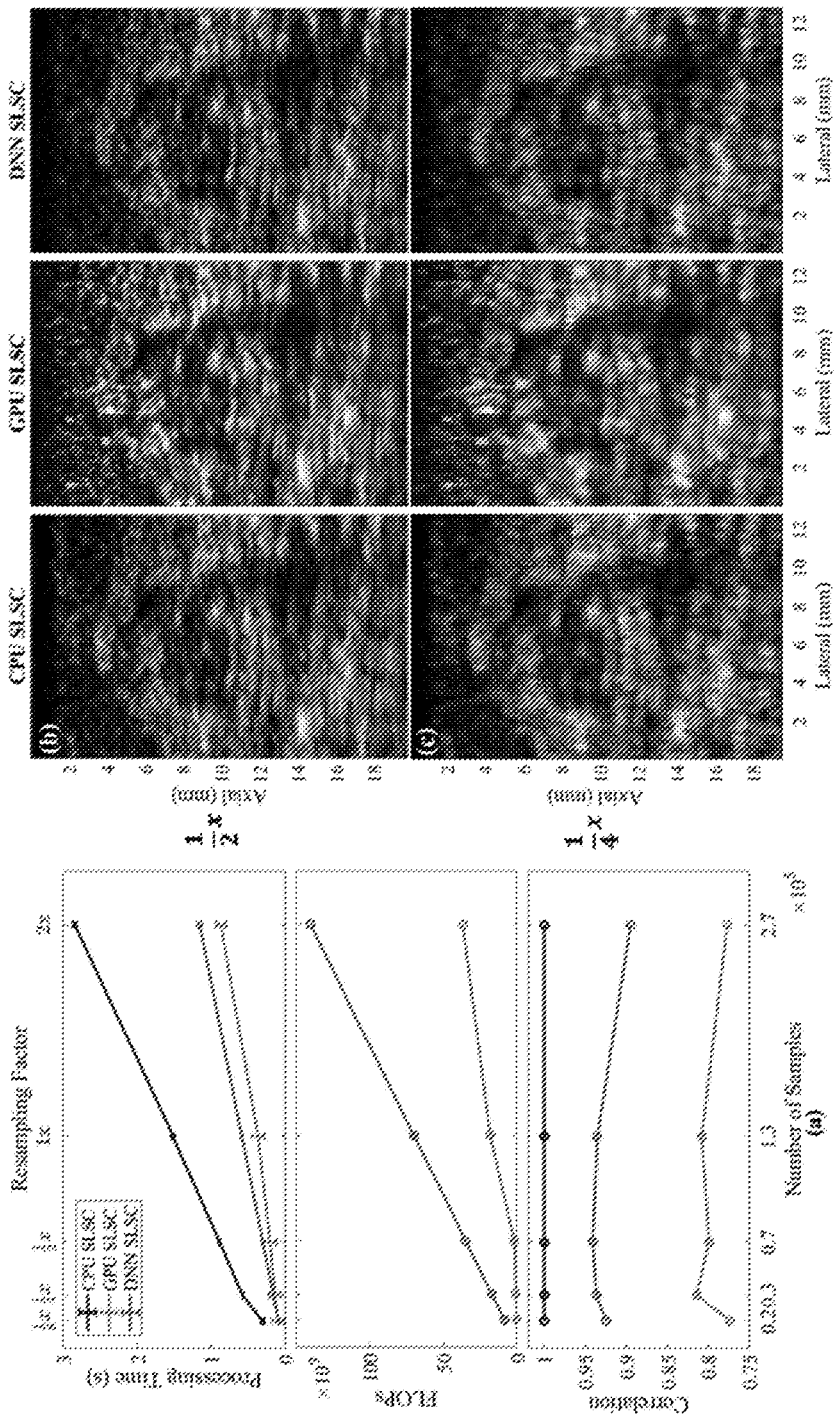
FIG. 6 illustrates processing times, floating-point operations (FLOPs), and image-to-image correlations as functions of the number of samples included in each SLSC implementation and example images demonstrating the ability of neural network-based SLSC images to match the SLSC image truths.
Figure 8:
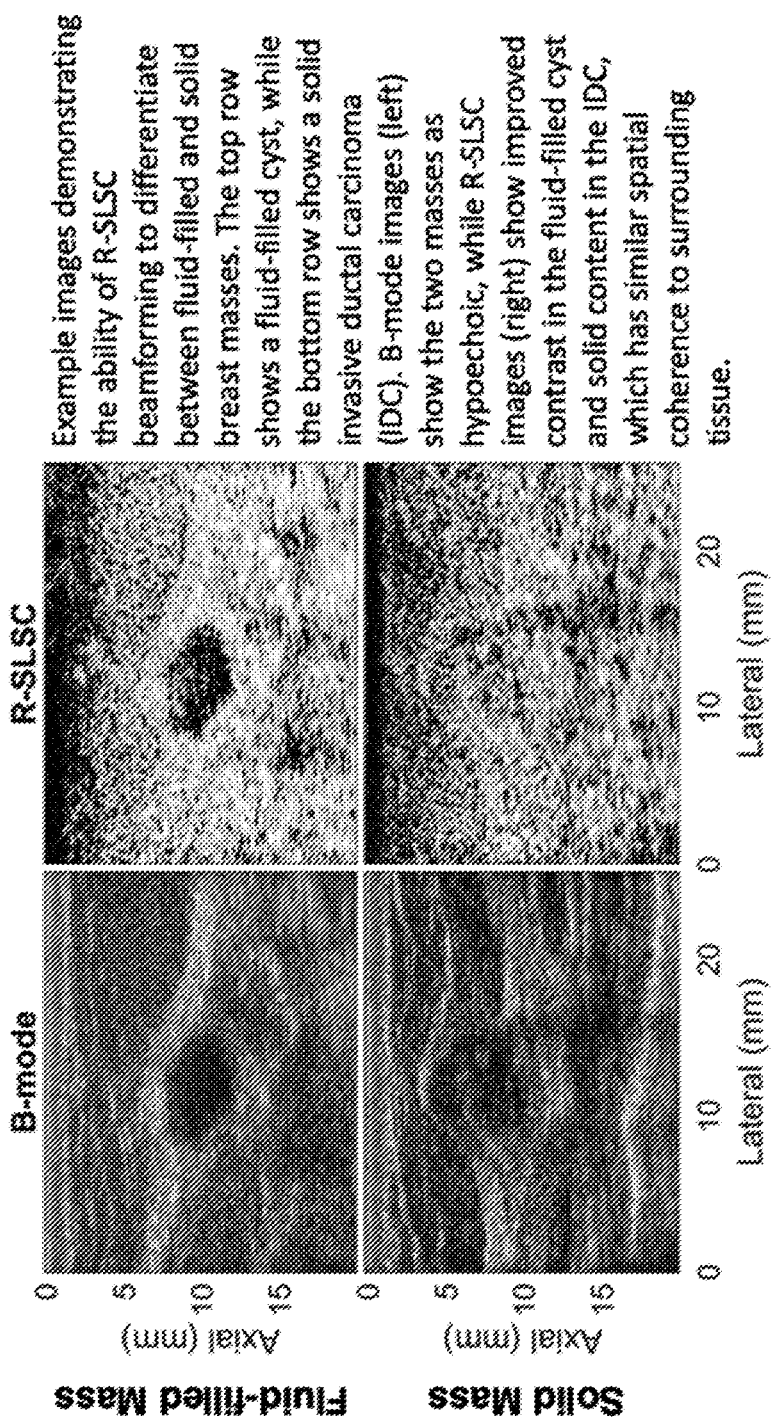
FIG. 8 illustrates example images demonstrating the ability of R-SLSC beamforming to differentiate between fluid-filled and solid breast masses.

SLSC images may improve the detection and differentiation between solid masses and fluid-filled masses from ultrasound images and may improve the image quality (e.g., in breast, cardiac, fetal, liver, and/or thyroid imaging) for example, as shown in FIG. 8. However, calculating spatial coherence functions for deriving SLSC images may require extensive time-consuming and computer resource-intensive processes to calculate and produce, as well as specialized hardware, which may be expensive and not readily available. Accordingly, aspects of the present disclosure may include a system and/or method that uses deep neural networks (DNNs), artificial intelligence (AI), and/or machine learning techniques to infer spatial coherence functions, rather than calculating the spatial coherence functions, thereby reducing the level of time and computing resources required to obtain a spatial coherence function. In this way, more medical professionals and organizations may obtain spatial coherence functions (e.g., for deriving SLSC images), thereby improving medical diagnosis and treatment, reducing the number of unnecessary biopsies, reducing patient anxiety, and saving resources in the healthcare system. In addition, the neural network-based SLSC image may be more similar to the original SLSC algorithm both qualitatively and quantitatively, resulting in reduced estimation error compared to other implementations (e.g., as shown in FIG. 6). The coherence function may also be used to determine the content of the source of the operational input sample. As an example, the coherence function may be used to directly differentiate solid masses from fluid-filled masses without requiring the formation of an SLSC image (e.g., as shown in FIGS. 5A and 5B). As another example, some sources (e.g., clutter, noise, etc.) may have similar coherence function characteristics to fluid masses. Therefore, these sources may similarly be distinguished from tissue, which may have similar coherence function characteristics to solid masses.

As described herein, aspects of the present disclosure may include a training process for training a neural network to produce spatial coherence functions based on a set of input samples. For example, the training process may involve receiving an input sample, receiving a coherence function truth associated with the input sample, storing information mapping the coherence function truth to the input sample, and repeating this process for any number of input samples and associated coherence function truths. In some embodiments, aspects of the present disclosure may refine the neural network using any variety of suitable techniques (e.g., back-propagation, weightings adjustments, etc.). In this way, a neural network may be trained, updated, and refined over a period of time and thus, may be used to infer a variety of coherence functions associated with different sets of input samples (e.g., ultrasound image data, etc.). For example, in a runtime setting, aspects of the present disclosure may receive input sample data (e.g., ultrasound image data), apply the sample data to the trained neural network, and obtain a coherence function from the trained neural network which identifies the coherence function mapped to the sample data. In this way, the coherence function may be quickly obtained without the need for time-consuming and computer resource-intensive calculations.

While the systems and/or methods, described herein, may discuss a technique for inferring spatial coherence functions for deriving SLSC images, it will be appreciated that the systems and/or methods are not so limited. For example, spatial coherence functions may be used in a variety of coherence-based beamforming applications, including any type of application that uses a correlation estimate, such as motion detection from ultrasound data, motion detection from photoacoustic data, blood-flow estimation, sound speed correction, speckle tracking, elastography, minimum variance beamforming, coherence-weighted imaging, and/or other advanced beamforming techniques (e.g., advanced ultrasound-based reconstruction techniques). That is, aspects of the present disclosure may improve the manner in which spatial coherence functions are obtained, and once obtained, the spatial coherence functions may be used for any variety of applications. Also, any variety of input sample data may be used to train a neural network and use the trained neural network in runtime. For example, the input sample data may include axial kernel data from ultrasound channel data, samples corresponding to a single axial position in space received by multiple ultrasound system channels, an entire recorded channel data set, all axial positions for a lateral line, or multiple recordings over a period of time.

Embodiments of the disclosure may include a system, a method, and/or a computer program product at any possible technical detail level of integration. The computer program product may include a computer readable storage medium (or media) having computer readable program instructions thereon for causing a processor to carry out aspects of the present disclosure.

FIG. 1 illustrates an example overview of an example implementation as described herein. More specifically, FIG. 1 illustrates an example process for using a trained neural network to infer a coherence function from a set of input sample data (e.g., ultrasound channel data). As shown in FIG. 1, ultrasound channel data may be received (e.g., from an ultrasound imaging device). Delays may be applied to focus separate channels of the ultrasound data and to focus energy at specific points in the image. As understood to those with ordinary skill in the art, a delay and sum (DAS) image may be formed after applying the delays. Alternatively, an SLSC image may be derived from a coherence function (e.g., by performing coherence calculations). In accordance with aspects of the present disclosure, a trained neural network may be used to infer the coherence function, rather than computer-intensive operations. For example, as shown in FIG. 1, an input axial kernel may be formed from the ultrasound channel data, after applying the delays. In some embodiments, there may be multiple axial kernels each representing multiple lateral and axial position data received by multiple channels. The input axial kernel data may be inputted to the trained neural network.

In some embodiments, the neural network may be modeled after the mathematical cross-correlation function including an input layer followed by four fully connected layers and an average pooling layer, with a rectified linear unit (ReLU) activation function for the first three fully connected layers, and a hyperbolic tangent (tanh) activation function on the final fully connected layer in order to limit the output of the neural network between −1 and 1, similar to the mathematical cross-correlation function (e.g., as shown in FIGS. 7, and 9A-9C). The first dimension of the size of each neural network layer may match the number of axial samples contained within the input axial kernel data, until the final layer of the neural network where the size may be compressed through the average pooling operation. Using the trained neural network, a coherence function mapped to the input axial kernel data may be obtained. This coherence function may then be used to form an SLSC image after a suitable summation process (e.g., also referred to as a DNN SLSC image). One example of a summation process may be achieved according to the equation:

$$R_{sl} = \int_1^M \hat{R}(m)dm \approx \Sigma_{m=1}^M \hat{R}(m) \quad (1)$$

where $R_{sl}$ is the SLSC image pixel value, M is the short-lag value, $\hat{R}(m)$ is the coherence function, and m is equally spaced elements or lags. This SLSC image may be presented to medical professionals in the form of an image overlay or duplex mode enabling examination of features of interest using the traditional DAS image followed by overlay of the SLSC image, providing further insight into the presence of solid mass contents or clutter reduction in fluid-filled masses. As another example, different combinations of the summation process may occur to form other types of images based on the SLSC image. For example, a robust SLSC (R-SLSC) image may be formed by vectorizing and stacking coherence images, performing robust principal component analysis (RPCA) to denoise the images, followed by a weighted summation of coherence images to form an R-SLSC image. In another example, a locally-weighted SLSC (LW-SLSC) image may be formed by computing weighted coefficients obtained by minimizing the total variation of the weighted sum within a kernel that considers multiple axial and lateral spatial positions and lag values, then applying an optimized weighted summation to coherence functions.

Figure 2:
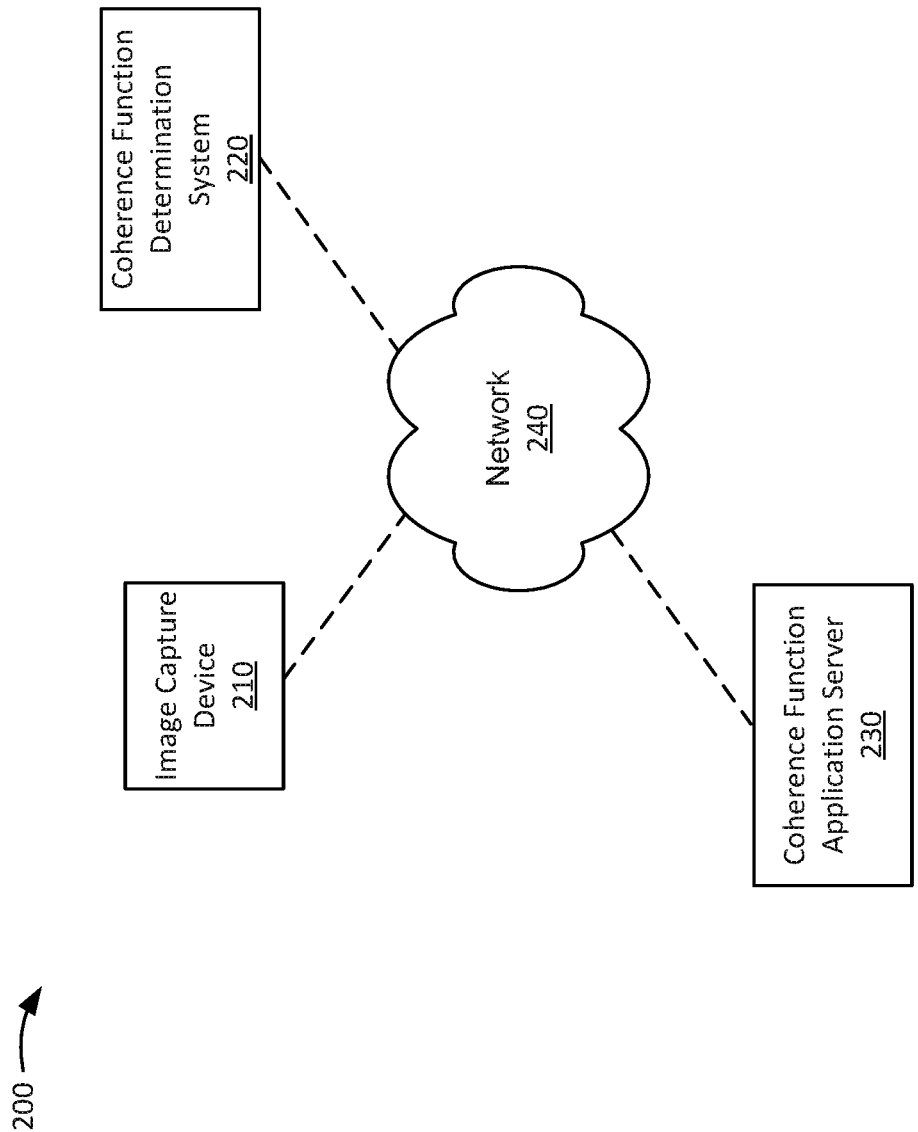
FIG. 2 illustrates an example environment as described herein.

FIG. 2 illustrates an example environment in accordance with aspects of the present disclosure. As shown in FIG. 2, environment 200 includes an image capture device 210, a coherence function determination system 220, a coherence function application server 230, and a network 240.

The image capture device 210 may include any variety of one or more medical or non-medical imaging devices. In one example embodiment, the image capture device 210 may include an ultrasound imaging device. The image capture device 210 may be used to capture an image (e.g., an ultrasound image) of a patient. In some embodiments, the image capture device 210 may provide image data to the coherence function determination system 220.

The coherence function determination system 220 may include one or more computing devices that maintains a neural network (e.g., a deep neural network) for inferring or determining coherence functions (e.g., spatial coherence functions) based on a set of input sample data (e.g., ultrasound image data received from the image capture device 210, axial kernel data derived from ultrasound image data, or any other variety of sample data). In this way, the coherence function may be determined using the trained neural network without the need to perform time consuming and computer resource-intensive calculations to determine the coherence function.

The coherence function application server 230 may include one or more computing devices that uses a coherence function (e.g., obtained by the coherence function determination system 220) for any variety of applications. For example, from the coherence function, the coherence function application server 230 may generate an SLSC image and/or a R-SLSC image and/or an LW-SLSC image. Additionally, or alternatively, the coherence function application server 230 may use the coherence function for any type of application that uses a correlation estimate, such as motion detection from ultrasound data, motion detection from photoacoustic data, blood-flow estimation, sound speed correction, speckle tracking, elastography, minimum variance beamforming, coherence-weighted imaging, and/or other advanced beamforming techniques (e.g., advanced ultrasound-based reconstruction techniques). That is to say, the coherence function application server 230 may host any variety of applications that use the coherence function obtained by the coherence function determination system 220. As the coherence function determination system 220 may obtain coherence functions more quickly and with fewer resources using a trained neural network, the access to applications hosted by the coherence function application server 230 may be improved.

The network 240 may include network nodes and one or more wired and/or wireless networks. For example, the network 240 may include a cellular network (e.g., a second generation (2G) network, a third generation (3G) network, a fourth generation (4G) network, a fifth generation (5G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, the network 240 may include a local area network (LAN), a wide area network (WAN), a metropolitan network (MAN), the Public Switched Telephone Network (PSTN), an ad hoc network, a managed Internet Protocol (IP) network, a virtual private network (VPN), an intranet, the Internet, a fiber optic-based network, and/or a combination of these or other types of networks. In some embodiments, the network 240 may include copper transmission cables, optical transmission fibers, wireless transmission, routers, firewalls, switches, gateway computers and/or edge servers.

The quantity of devices and/or networks in the environment 200 is not limited to what is shown in FIG. 2. In practice, the environment 200 may include additional devices and/or networks; fewer devices and/or networks; different devices and/or networks; or differently arranged devices and/or networks than illustrated in FIG. 2. Also, in some implementations, one or more of the devices of the environment 200 may perform one or more functions described as being performed by another one or more of the devices of the environment 200. Devices of the environment 200 may interconnect via wired connections, wireless connections, or a combination of wired and wireless connections.

Figure 3:
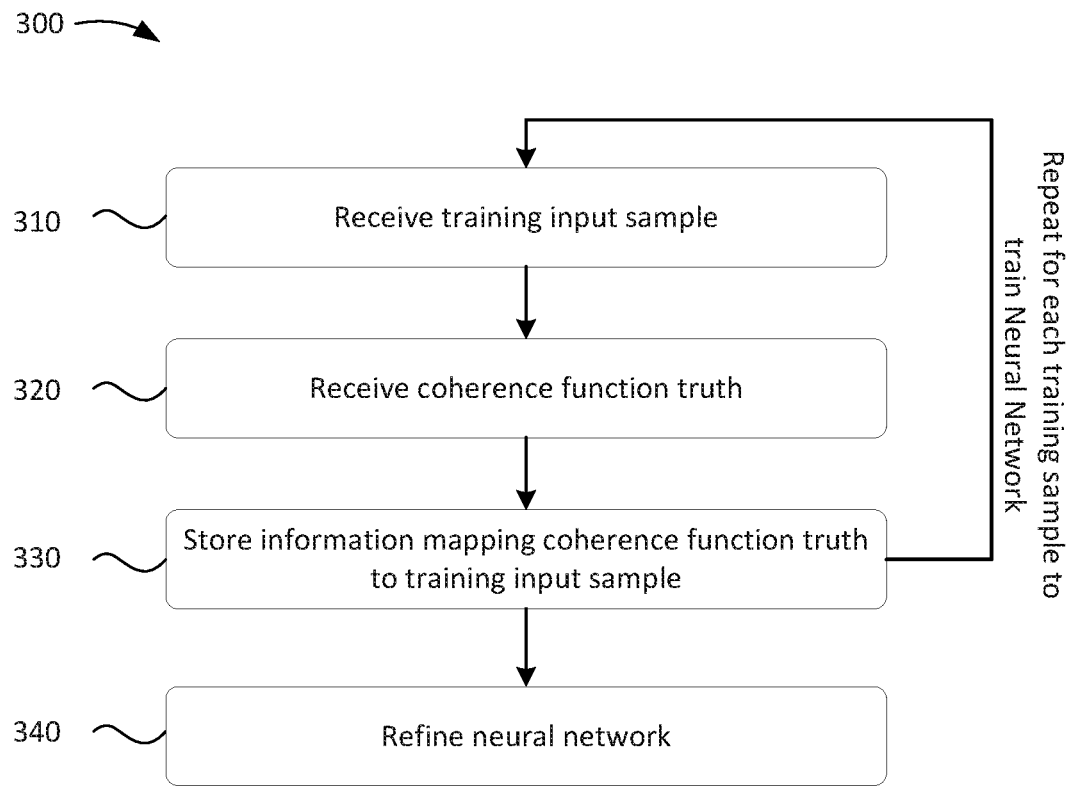
FIG. 3 illustrates an example flowchart of a process for training a deep neural network to predict or determine a coherence function based on a set of input samples.

FIG. 3 illustrates an example flowchart of a process for training a deep neural network to predict or determine a coherence function based on a set of input samples. The blocks of FIG. 3 may be implemented in the environment of FIG. 2, for example, and are described using reference numbers of elements depicted in FIG. 2. As noted herein, the flowchart illustrates the architecture, functionality, and operation of possible implementations of systems, methods, and computer program products according to various embodiments of the present disclosure.

As shown in FIG. 3, The process 300 may include receiving a training input sample (block 310). For example, the coherence function determination system 220 may receive a training input sample, such as ultrasound image data, axial kernel data from ultrasound channel data, samples corresponding to a single axial position in space received by multiple ultrasound system channels, an entire recorded channel data, all axial positions for a lateral line, or multiple recordings over a period of time, or any other type of input sample data from which a coherence function may be derived. As described herein, the training input sample may include a sample in which a coherence function truth has been previously determined. For example, the training input sample may consist of in vivo breast data, which is known to be highly heterogeneous and therefore provides multiple variations of coherence function truths.

The process 300 also may include receiving a coherence function truth (block 320). For example, the coherence function determination system 220 may receive a coherence function truth linked to the training input sample. More specifically, the training input sample may include experimental data and/or historical data in which the coherence function truth has been previously determined or calculated (e.g., from an experiment and/or from any prior calculation of the coherence function).

The process 300 further may include storing information mapping the coherence function truth to the training input sample (block 330). For example, the coherence function determination system 220 may store information that maps the coherence function truth to the training input sample (e.g., in a data structure associated with the neural network and stored in a database). In some embodiments, the data structure may be in any variety of formats and may include a link that associated the coherence function truth to the input sample.

As further shown in FIG. 3, the process 300 may return to block 310 in which blocks 310-330 may be repeated for additional input samples and coherence function truths associated with each training input sample. In this way, the neural network may be trained to recognize, determine, and/or predict a variety of coherence functions associated with different input sample datasets. Thus, in operation, the trained neural network may be used to predict a coherence function based on an input sample. As an illustrative example, the trained neural network may be used to predict a coherence function based on ultrasound image data. In turn, this coherence function may be used to form an SLSC image. As described herein, the SLSC image may improve the detection and differentiation of solid masses from fluid-filled masses present in an ultrasound image, as shown in FIG. 8. The coherence function may also be used to directly differentiate solid masses from fluid-filled masses without requiring the formation of an SLSC image (e.g., as shown in FIG. 5A).

The process 300 also may include refining the neural network (block 340). For example, the coherence function determination system 220 may refine the neural network over a period of time and using any suitable neural network refinement technique. As one example, the coherence function determination system 220 may implement back propagation and adjust weights based on comparing a predicted coherence function to a calculated or measured coherence function truth. For example, the weighted mean squared error (MSE) between the predicted coherence function and a calculated or measured coherence function truth may be measured by placing a custom Gaussian weighting scheme according to the following equation:

$$MSE = \frac{1}{M} \sum_{m=1}^{M} w_m (y_m - \hat{y}_m)^2 \quad (2)$$

where m is the lag, $y_m$ is the neural network predicted coherence function, $\hat{y}_m$ is the ground truth coherence function, and w is a vector of Gaussian weights, which may have a mean of 0 and a standard deviation of 25.6. This weighted MSE refinement technique places a larger weight on errors in the short-lag region which is the region used to create SLSC images, and therefore the region most critical to improving SLSC image quality (e.g., as shown in FIG. 9B). In some embodiments, the neural network may be refined based on the output of an application that uses the coherence function and/or based on output coherence functions predicted by the trained neural network and measured coherence functions. Other refinement techniques may be employed as appropriate. With one or more refinement techniques, the accuracy of the coherence functions predictions made by the neural network may continuously improve, thereby improving the outputs of underlying applications that use the coherence functions.

In some embodiments, training the neural network may involve mapping multiple different sets of training input samples to respective coherence function truths, obtaining the coherence function by receiving information distinguishing solid and fluid mass contents, mapping the plurality of different sets of training input samples to the respective short-lag spatial coherence (SLSC) image truths, and/or refining the trained neural network based on output coherence functions predicted by the neural network and measured coherence functions.

Figure 4:
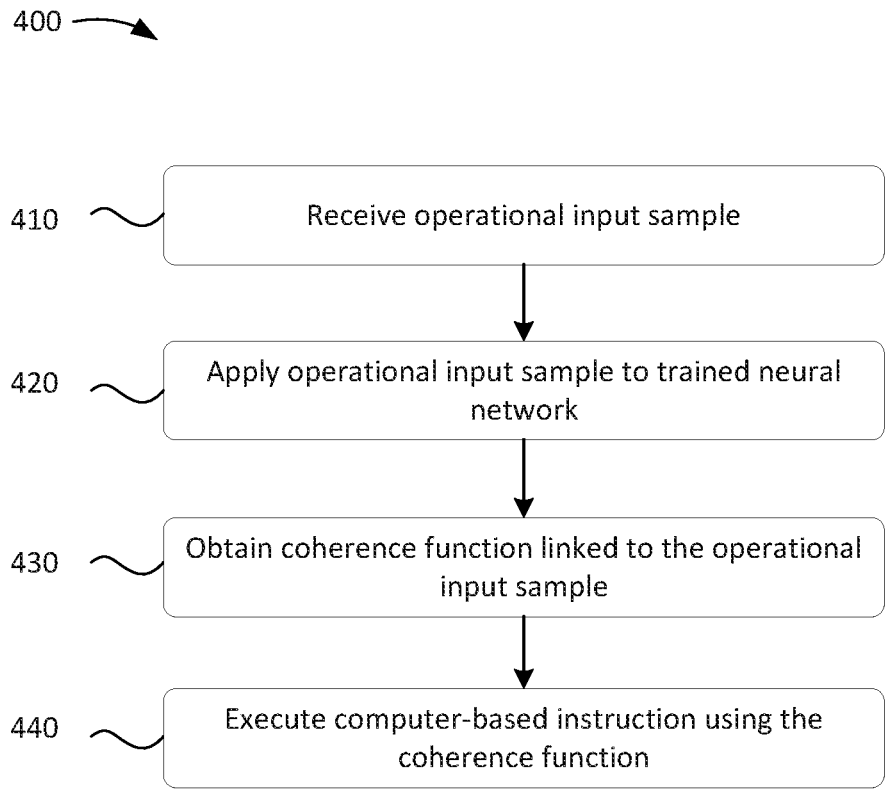
FIG. 4 illustrates an example flowchart of a process for using a trained neural network to obtain a coherence function based on input sample data.

FIG. 4 illustrates an example flowchart of a process for using a trained neural network to obtain a coherence function based on input sample data. The blocks of FIG. 4 may be implemented in the environment of FIG. 2, for example, and are described using reference numbers of elements depicted in FIG. 2. As noted herein, the flowchart illustrates the architecture, functionality, and operation of possible implementations of systems, methods, and computer program products according to various embodiments of the present disclosure.

As shown in FIG. 4, The process 400 may include receiving operational input sample data (block 410). For example, the coherence function determination system 220 may receive the operational input sample from the image capture device 210 and/or other source. In some embodiments, the operational input sample data may include ultrasound image data, axial kernel data from ultrasound channel data, samples corresponding to a single axial position in space received by multiple ultrasound system channels, an entire recorded channel data, all axial positions for a lateral line, or multiple recordings over a period of time, or any other type of input sample data from which a coherence function may be derived.

As described herein, unlike the training sample, the operational input sample may include source data for which the coherence function is not known, but is to be determined using a trained neural network (e.g., such that the coherence function may be obtained without the need for complex, time consuming, and resource-intensive calculations). As one illustrative example, the operational input sample may be axial kernel data derived from an ultrasound image received as part of a medical imaging process.

The process 400 also may include applying the operational input sample to a trained neural network (block 420). For example, the coherence function determination system 220 may apply the operational input sample (received at block 410) to a trained neural network (e.g., trained using the process 300 of FIG. 3). In some embodiments, the operational input sample may be processed or transformed prior to being applied to the neural network. As one example, the operational input sample may be ultrasound channel data and transformed to axial kernel data.

The process 400 further may include obtaining a coherence function linked to the operational input sample (block 430). For example, the coherence function determination system 220 may compare data from within the operational input sample to data stored within the trained neural network and identify a coherence function linked to the operational input sample. More specifically, the coherence function determination system 220 may identify training input sample data that matches the operational input sample data, and identify the coherence function linked to the matching training input sample data. This coherence function is determined to match the operational input sample. In this way, the coherence function may be determined using the trained neural network.

The process 400 also may include executing a computer-based instruction using the coherence function (block 440). For example, the coherence function determination system 220 may execute a computer-based instruction using the coherence function. In some embodiments, the computer-based instruction may include an instruction to store or output the coherence function to the coherence function application server 230 and to instruct the coherence function application server 230 to execute an application using the coherence function (e.g. an application to generate an SLSC image using the coherence function). Additionally, or alternatively, the computer-based instruction may include an instruction for the coherence function determination system 220 to execute an application itself using the coherence function. Additionally, or alternatively, the computer-based instruction may include an instruction for the coherence function determination system 220 to refine the trained neural network based on the output of the application that uses the coherence function. Other examples are possible, and in general, the coherence function determination system 220 may execute any variety of instructions, applications, or tasks using the coherence function (e.g., motion detection from ultrasound data, motion detection from photoacoustic data, blood-flow estimation, sound speed correction, speckle tracking, elastography, minimum variance beamforming, coherence-weighted imaging, and/or other advanced beamforming techniques (e.g., advanced ultrasound-based reconstruction techniques), etc.

In some embodiments, the trained neural network may also link input training samples not only to coherence functions, but also to an SLSC image itself. In this way, an SLSC image may be generated from an operational input sample while bypassing the coherence function altogether. In some embodiments, one or more operations of the coherence function determination system 220 may be integrated into a medical scanner. In this way, the medical scanner itself may be used to obtain a coherence function and generate an SLSC image. In some embodiments, the systems and/or methods, described herein, may be integrated into an automatic detection system that may automatically detect a solid mass vs. a fluid-filled mass using an SLSC image generated from a coherence function obtained using the trained neural network. In some embodiments, the trained neural network may also link an input sample to a discriminator value (e.g., lag-one coherence or coherence length) which may be used to automatically detect a solid mass vs. a fluid-filled mass.

FIGS. 5A and 5B illustrate one example use of the coherence function to directly distinguish between solid and fluid masses using properties or characteristics of the coherence function, specifically lag-one coherence (LOC) and coherence length (CL). LOC may be measured as the coherence function evaluated specifically at lag 1 and CL may be measured as the first zero-crossing of the coherence function. LOC and CL may be parameterized and a threshold may be set to measure sensitivity and specificity of fluid-filled mass detection. With these measurements, a receiver operating characteristic (ROC) curve may be used to compare both LOC and CL and an optimal threshold may be determined by measuring the distance to the ideal operating point of (0,1). As shown in FIGS. 5A and 5B, LOC and CL may improve the sensitivity and/or specificity of fluid-filled mass detection compared to medical professionals when using only B-mode images or the combination of B-mode and R-SLSC images. As an example, when analyzing data from 23 masses total (i.e., 16 solid masses, 7 fluid-filled masses) and the LOC threshold was set to 0.3, the sensitivity was 100% and the specificity was 94% for fluid-filled mass detection. For these same data, when the CL threshold was set to 6, the sensitivity was 100% and the specificity was 87% for fluid-filled mass detection. The results of the medical professionals represented as data points in FIG. 5A were specifically obtained from five board-certified radiologists with between 1 and 22 years of experience reading breast ultrasound images.

FIG. 6 illustrates one example result of processing times, FLOPs, and image-to-image correlations as functions of the number of samples included in each SLSC implementation including the original SLSC algorithm (e.g., also referred to as CPU SLSC), a graphics processer unit (GPU) SLSC implementation (e.g., also referred to as GPU SLSC), and the neural network-based SLSC implementation (e.g., also referred to as DNN SLSC). In this illustrative example, the DNN SLSC image was generated by inputting axial kernel data into the neural network, receiving the associated coherence function, and summing the coherence function up to lag 5 resulting in the DNN SLSC pixel value. This process was then repeated for each axial and lateral position in the image. Identical summation and image formation processes were implemented after obtaining the coherence functions with the CPU and GPU implementations.

As shown in FIG. 6, both GPU SLSC and DNN SLSC may have similarly improved computational speed as the number of samples decreases. With 128 lateral samples and 130 axial samples, which corresponds to approximately $0.2 \times 10^5$ samples total, the minimum processing times for CPU, GPU, and DNN SLSC are 0.31, 0.09, and 0.09 s, respectively, corresponding to frame rates of 3, 11, and 11 Hz, respectively. In addition, as shown in FIG. 6, the corresponding FLOP results show that DNN SLSC may require more FLOPs than GPU SLSC for each resampling factor, however the increased number of FLOPs may not directly translate to an increase in processing time, considering that the processing times for GPU SLSC and DNN SLSC with less than or equal to $0.7 \times 10^5$ samples are comparable. Although FLOPs may be representative of computational complexity, processing time may be a better representation of computational speed because SLSC is ultimately intended to be a real-time imaging method.

As shown in FIG. 6, DNN SLSC images may provide a better quantitative match to the CPU SLSC image truths compared to the GPU SLSC images as demonstrated in the image-to-image correlations, indicating that DNN SLSC may provide reduced estimation error compared to GPU SLSC which may be because the neural network is trained to mimic the coherence function, particularly in short-lag regions, which may allow the neural network to inherently correct for errors in floating point values. In addition, as shown in FIG. 6, DNN SLSC images may provide a better qualitative match to the CPU SLSC image truths compared to the GPU SLSC images, as demonstrated by the example images in FIG. 6.

FIG. 7 illustrates an example architecture of a neural network, in accordance with aspects of the present disclosure. As shown in FIG. 7, in some embodiments, the neural network may be modeled after the mathematical cross-correlation function including an input layer followed by four fully connected layers and an average pooling layer, with a rectified linear unit (ReLU) activation function for the first three fully connected layers, and a hyperbolic tangent (tanh) activation function on the final fully connected layer in order to limit the output of the neural network between −1 and 1, similar to the mathematical cross-correlation function. In addition, as shown in FIG. 7, the first dimension of the size of each neural network layer may match the number of axial samples contained within the input axial kernel data, until the final layer of the neural network where the size may be compressed through the average pooling operation.

FIG. 8 illustrates example images demonstrating the ability of R-SLSC beamforming to differentiate between fluid-filled and solid breast masses. The top row shows a solid invasive ductal carcinoma (IDC). B-mode images (shown on the left) show the two masses as hypoechoic, meaning darker than the surrounding tissue, while R-SLSC images (shown on the right) show improved contrast in the fluid-filled cyst and solid content in the IDC, which has similar spatial coherence to surrounding tissue.

FIGS. 9A, 9B, and 9C illustrate example coherence function truths and coherence functions generated by the trained neural network. As shown in FIG. 9A, the neural network generated coherence function output matches within a threshold of the coherence function truth. In another illustrative example, FIG. 9B shows a region where the neural network generated coherence function is smoother compared to the truth and the best match with the truth is obtained at lags less than or equal to 25 as a result of the Gaussian weighted mean square error loss function. The MSE difference between these two functions is 0.02, however when considering the region where penalties for mismatch was larger in the regions less than or equal to lag 25, the MSE is 0.002. Otherwise, for lags greater than 25, the MSE is 0.03. In another illustrative example, FIG. 9C shows coherence function outputs averaged over multiple axial and lateral positions, specifically the mean±the standard deviation of coherence functions within a 1 mm×1 mm region surrounding the focus of in vivo breast data.

Figure 10:
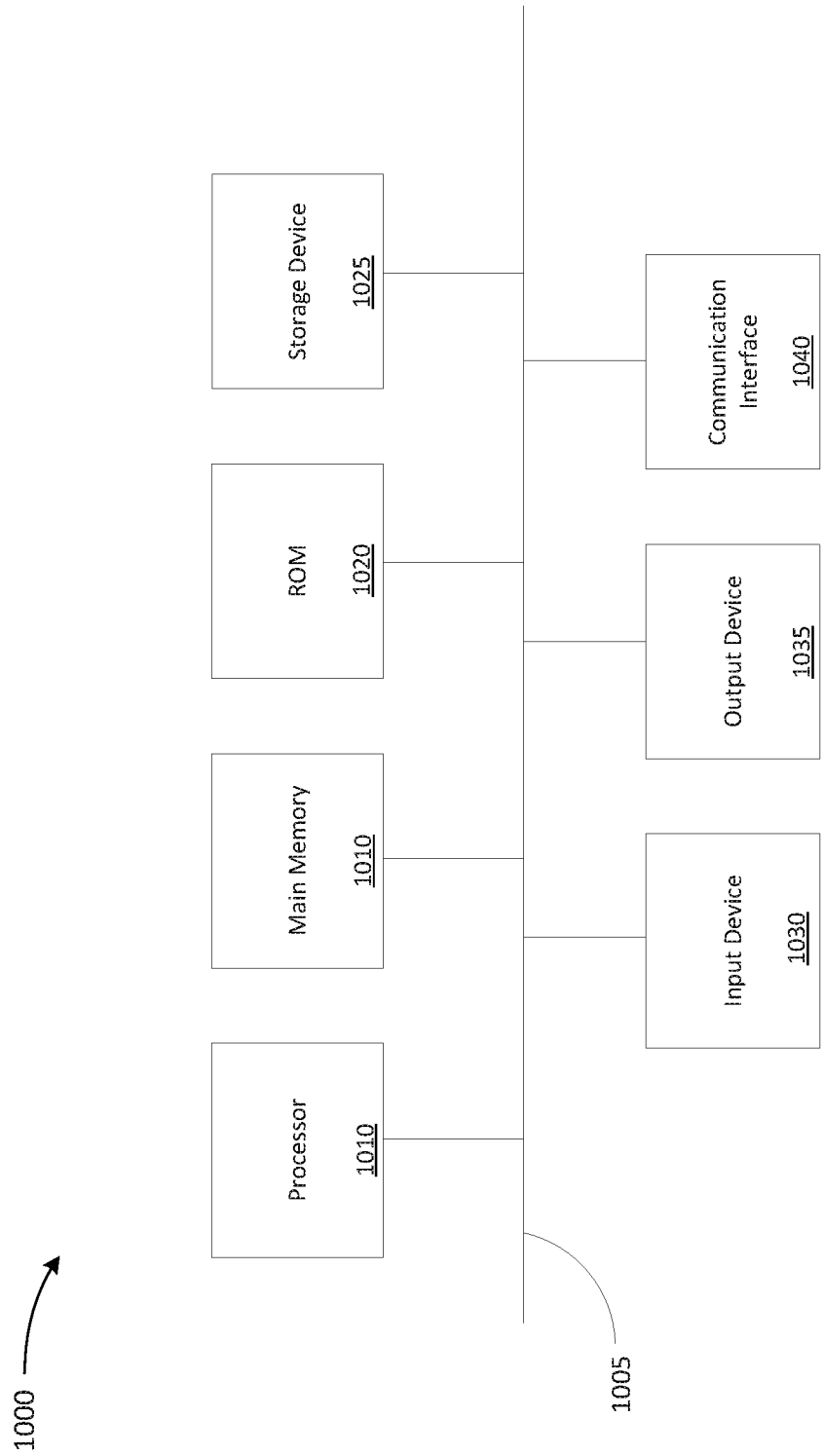
FIG. 10 illustrates example components of a device that may be used within environment of FIG. 2.

FIG. 10 illustrates example components of a device 1000 that may be used within environment 200 of FIG. 2. Device 1000 may correspond to the image capture device 210, the coherence function determination system 220, and/or the coherence function application server 230. Each of the image capture device 210, the coherence function determination system 220, and/or the coherence function application server 230 may include one or more devices 1000 and/or one or more components of device 1000.

As shown in FIG. 10, device 1000 may include a bus 1005, a processor 1010, a main memory 1015, a read only memory (ROM) 1020, a storage device 1025, an input device 1030, an output device 1035 and a communication interface 1040.

Bus 1005 may include a path that permits communication among the components of device 1000. Processor 1010 may include a processor, a microprocessor, an application specific integrated circuit (ASIC), a field programmable gate array (FPGA), or another type of processor that interprets and executes instructions. Main memory 1020 may include a random access memory (RAM) or another type of dynamic storage device that stores information or instructions for execution by processor 1010. ROM 1020 may include a ROM device or another type of static storage device that stores static information or instructions for use by processor 1010. Storage device 1025 may include a magnetic storage medium, such as a hard disk drive, or a removable memory, such as a flash memory.

Input device 1030 may include a component that permits an operator to input information to device 1000, such as a control button, a keyboard, a keypad, or another type of input device. Output device 1035 may include a component that outputs information to the operator, such as a light emitting diode (LED), a display, or another type of output device. Communication interface 1040 may include any transceiver-like component that enables device 1000 to communicate with other devices or networks. In some implementations, communication interface 1040 may include a wireless interface, a wired interface, or a combination of a wireless interface and a wired interface. In some embodiments, communication interface 1040 may receive computer readable program instructions from a network and may forward the computer readable program instructions for storage in a computer readable storage medium (e.g., storage device 1025).

Device 1000 may perform certain operations, as described in detail below. Device 1000 may perform these operations in response to processor 1010 executing software instructions contained in a computer-readable medium, such as main memory 1015. A computer-readable medium may be defined as a non-transitory memory device and is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. A memory device may include memory space within a single physical storage device or memory space spread across multiple physical storage devices.

The software instructions may be read into main memory 1015 from another computer-readable medium, such as storage device 1025, or from another device via communication interface 1040. The software instructions contained in main memory 1015 may direct processor 1010 to perform processes that will be described in greater detail herein. Alternatively, hardwired circuitry may be used in place of or in combination with software instructions to implement processes described herein. Thus, implementations described herein are not limited to any specific combination of hardware circuitry and software.

In some implementations, device 1000 may include additional components, fewer components, different components, or differently arranged components than are shown in FIG. 10.

In accordance with aspects of the present disclosure, a neural network trained in software may be implemented in hardware (e.g., one or more FPGAs) associated with a computing device to perform operations. In some embodiments, aspects of the present disclosure may be used in miniaturized or low-power devices. For example, FPGAs may be used to implement neural networks with low energy consumption per FLOP at lower computational cost than GPU implementations. These low-power implementations may be used in embedded system applications (e.g., in remote areas of the world, where high-energy computing is not feasible). Also, aspects of the present disclosure may provide a low-power neural network-based FPGA implementations for miniaturized imaging systems. In addition, as shown in FIG. 6, the stable processing times of the neural network improve performance in applications requiring synchronization with consistent and predictable frame rates.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the disclosure may include a system, a method, and/or a computer program product at any possible technical detail level of integration. The computer program product may include a computer readable storage medium (or media) having computer readable program instructions thereon for causing a processor to carry out or execute aspects and/or processes of the present disclosure.

In some embodiments, the computer readable program instructions may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on a user's computer, partly on the user's computer, as a stand-alone software package, partly on the user's computer and partly on a remote computer or entirely on the remote computer or server.

In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

In embodiments, a service provider could offer to perform the processes described herein. In this case, the service provider can create, maintain, deploy, support, etc., the computer infrastructure that performs the process steps of the disclosure for one or more customers. These customers may be, for example, any business that uses technology. In return, the service provider can receive payment from the customer(s) under a subscription and/or fee agreement and/or the service provider can receive payment from the sale of advertising content to one or more third parties.

The foregoing description provides illustration and description, but is not intended to be exhaustive or to limit the possible implementations to the precise form disclosed. Modifications and variations are possible in light of the above disclosure or may be acquired from practice of the implementations.

It will be apparent that different examples of the description provided above may be implemented in many different forms of software, firmware, and hardware in the implementations illustrated in the figures. The actual software code or specialized control hardware used to implement these examples is not limiting of the implementations. Thus, the operation and behavior of these examples were described without reference to the specific software code—it being understood that software and control hardware can be designed to implement these examples based on the description herein.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

While the present disclosure has been disclosed with respect to a limited number of embodiments, those skilled in the art, having the benefit of this disclosure, will appreciate numerous modifications and variations there from. It is intended that the appended claims cover such modifications and variations as fall within the true spirit and scope of the disclosure.

No element, act, or instruction used in the present application should be construed as critical or essential unless explicitly described as such. Also, as used herein, the article "a" is intended to include one or more items and may be used interchangeably with "one or more." Where only one item is intended, the term "one" or similar language is used. Further, the phrase "based on" is intended to mean "based, at least in part, on" unless explicitly stated otherwise.

What is claimed is:

1. A computer-implemented method comprising:
   training a neural network by mapping a plurality of different sets of training input samples to respective spatial coherence function truths to generate a trained neural network;
   receiving an operational input sample;
   inputting the operational input sample into the trained neural network;
   obtaining, from the trained neural network, a spatial coherence function mapped to the operational input sample in response to the inputting the operational input sample into the trained neural network, wherein the spatial coherence function is usable to form an image according to $R_{sl}=\int_1^M \hat{R}(m)dm$, where $R_{sl}$ represents an image pixel value, M represents a short-lag value, and $\hat{R}(m)$ represents the spatial coherence function; and
   executing a computer-based instruction based on obtaining the spatial coherence function.

2. The method of claim 1, wherein the operational input sample data includes at least one selected from the group consisting of:
   axial kernel data from ultrasound or ultrasound-derived channel data;
   samples corresponding to a single axial position in space received by multiple ultrasound system channels;
   an entire recorded channel data set; and
   all axial positions for a lateral line, or multiple recordings over a period of time.

3. The method of claim 1, wherein the inputting the operational input sample data into the trained neural network comprises transforming the operational input sample data into input axial kernel data.

4. The method of claim 3, wherein the input axial kernel data is associated with ultrasound or photoacoustic or ultrasound-derived channel data.

5. The method of claim 1, wherein executing the computer-based instruction includes at least one selected from the group consisting of:
   an instruction to store or output the spatial coherence function;
   an instruction to execute an application using the spatial coherence function, wherein the application includes at least one selected from the group consisting of:
   motion detection from ultrasound data,
   motion detection from photoacoustic data,
   blood-flow estimation,
   sound speed correction, speckle tracking,
   elastography, minimum variance beamforming, and coherence-weighted imaging, or advanced correlation-based beamforming techniques; and
   an instruction to refine the trained neural network based on the output of the application that uses the spatial coherence function.

6. The method of claim 1, wherein the training the neural network further comprises mapping respective short-lag spatial coherence (SLSC) image truths to the plurality of different sets of training input samples, the method further comprising obtaining an SLSC image mapped to the operational input sample in response to the inputting the operational input sample into the trained neural network.

7. The method of claim 1, further comprising refining the trained neural network based on output spatial coherence functions predicted by the neural network and measured spatial coherence functions.

8. A non-transitory computer readable storage medium having program instructions embodied therewith, the program instructions executable by a computing device to cause the computing device to perform operations comprising:
   receiving an operational input sample;
   inputting the operational input sample into a trained neural network;
   obtaining, from the trained neural network, a spatial coherence function mapped to the operational input sample in response to the inputting the operational input sample into the trained neural network, wherein the spatial coherence function is usable to form an image according to $R_{sl}=\int_1^M \hat{R}(m)dm$, where $R_{sl}$ represents an image pixel value, M represents a short-lag value, and $\hat{R}(m)$ represents the spatial coherence function; and
   executing a computer-based instruction based on obtaining the spatial coherence function.

9. The non-transitory computer readable storage medium of claim 8, wherein the operational input sample data includes at least one selected from the group consisting of:
   axial kernel data from ultrasound or ultrasound-derived channel data;
   samples corresponding to a single axial position in space received by multiple ultrasound system channels;
   an entire recorded channel data set; and
   all axial positions for a lateral line, or multiple recordings over a period of time.

10. The non-transitory computer readable storage medium of claim 8, wherein inputting the operational input sample data into the trained neural network comprised transforming the operational input sample data into input axial kernel data.

11. The non-transitory computer readable storage medium of claim 10, wherein the input axial kernel data is associated with ultrasound or photoacoustic or ultrasound-derived channel data.

12. The non-transitory computer readable storage medium of claim 8, wherein the executing the computer-based instruction includes at least one selected from the group consisting of:
   an instruction to store or output the spatial coherence function;
   an instruction to execute an application using the spatial coherence function, wherein the application includes at least one selected from the group consisting of:
   motion detection from ultrasound data,
   motion detection from photoacoustic data,
   blood-flow estimation,
   sound speed correction, speckle tracking,
   elastography, minimum variance beamforming, and coherence-weighted imaging, or advanced correlation-based beamforming techniques; and
   an instruction to refine the trained neural network based on the output of the application that uses the spatial coherence function.

13. The non-transitory computer readable storage medium of claim 8, wherein the operations further comprise at least one selected from the group consisting of:

training the neural network by mapping a plurality of different sets of training input samples to respective spatial coherence function truths or mapping respective short-lag spatial coherence (SLSC) image truths to the plurality of different sets of training input samples;

obtaining an SLSC image mapped to the operational input sample in response to the inputting the operational input sample into the trained neural network;

refining the trained neural network based on output spatial coherence functions predicted by the trained neural network and measured spatial coherence functions.

14. A system comprising:
a processor, a computer readable memory, a non-transitory computer readable storage medium associated with a computing device, and program instructions executable by the computing device to cause the computing device to perform operations comprising:
receiving an operational input sample;
inputting the operational input sample into a trained neural network that maps a plurality of different sets of input samples to one or more spatial coherence functions;
obtaining, from the trained neural network, a spatial coherence function mapped to the operational input sample in response to the inputting the operational input sample into the trained neural network, wherein the spatial coherence function is usable to form an image according to $R_{sl} = \int_1^M \hat{R}(m)dm$, where $R_{sl}$ represents an image pixel value, M represents a short-lag value, and $\hat{R}(m)$ represents the spatial coherence function; and
executing a computer-based instruction based on obtaining the spatial coherence function.

15. The system of claim 14, wherein the operational input sample data includes at least one selected from the group consisting of:
axial kernel data from ultrasound or ultrasound-derived channel data;
samples corresponding to a single axial position in space received by multiple ultrasound system channels;
an entire recorded channel data set; and
all axial positions for a lateral line, or multiple recordings over a period of time.

16. The system of claim 14, wherein the inputting the operational input sample data into the trained neural network comprised transforming the operational input sample data into input axial kernel data.

17. The system of claim 16, wherein the input axial kernel data is associated with ultrasound or ultrasound-derived channel data.

18. The system of claim 14, wherein the executing the computer-based instruction includes at least one selected from the group consisting of
an instruction to store or output the spatial coherence function;
an instruction to execute an application using the spatial coherence function, wherein the application includes at least one selected from the group consisting of:
motion detection from ultrasound data,
motion detection from photoacoustic data,
blood-flow estimation,
sound speed correction, speckle tracking,
elastography, minimum variance beamforming, and
coherence-weighted imaging, or advanced correlation-based beamforming techniques; and
an instruction to refine the trained neural network based on the output of the application that uses the spatial coherence function.

19. The system of claim 14, wherein the operations further comprise at least one selected from the group consisting of:
training the neural network by mapping a plurality of different sets of training input samples to respective spatial coherence function truths;
training the neural network by mapping the plurality of different sets of training input samples to the respective short-lag spatial coherence (SLSC) image truths;
obtaining an SLSC image mapped to the operational input sample in response to the inputting the operational input sample into the trained neural network;
refining the trained neural network based on output spatial coherence functions predicted by the neural network and measured spatial coherence functions.

20. The system of claim 14, wherein the operations further comprise determining the content of the source of the operational input sample.

* * * * *